US00PP18852P2

(12) United States Plant Patent
Meyer

(10) Patent No.: US PP18,852 P2
(45) Date of Patent: May 27, 2008

(54) **GUINEA *IMPATIENS* PLANT NAMED 'BALCELIMPUR'**

(50) Latin Name: *Impatiens hawkeri*
Varietal Denomination: Balcelimpur

(75) Inventor: Kerry M. Meyer, St. Thomas, MO (US)

(73) Assignee: Ball Horticultural Company, West Chicago, IL (US)

( * ) Notice: Subject to any disclaimer, the term of this patent is extended or adjusted under 35 U.S.C. 154(b) by 67 days.

(21) Appl. No.: 11/602,815

(22) Filed: Nov. 21, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Annette H Para
(74) *Attorney, Agent, or Firm*—Audrey Charles

(57) ABSTRACT

A new and distinct cultivar of New Guinea *Impatiens* plant named 'Balcelimpur', characterized by its single type medium purple-colored flowers, medium green-colored foliage, and vigorous, upright-mounded growth habit.

1 Drawing Sheet

Latin name of genus and species of plant claimed: *Impatiens hawkeri.*
Variety denomination: 'Balcelimpur'.

BACKGROUND OF THE INVENTION

The present invention relates to a new and distinct cultivar of New Guinea *Impatiens* plant botanically known as *Impatiens hawkeri* and hereinafter referred to by the cultivar name 'Balcelimpur'.

The new cultivar originated in a controlled breeding program in Arroyo Grande, Calif. during May 2002. The objective of the breeding program was the development of New Guinea *Impatiens* cultivars with numerous large flowers, attractive flower coloration, and a freely basal branching growth habit.

The new New Guinea *Impatiens* cultivar is the result of cross-pollination. The female (seed) parent of the new cultivar is Harmony Lavender Purple 'Danharpl', U.S. Plant Pat. No. 12,094, characterized by its single type medium red-purple-colored flowers, dark green-colored foliage, and compact growth habit. The male (pollen) parent of the new cultivar is Celebration 'Raspberry Rose', U.S. Plant Pat. No. 9,212, characterized by its single type dark rose-colored flowers, medium green-colored foliage, and upright growth habit. The new cultivar was discovered and selected as a single flowering plant within the progeny of the above stated cross-pollination during October 2002 in a controlled environment at Arroyo Grande, Calif.

Asexual reproduction of the new cultivar by terminal stem cuttings since October 2002 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcelimpur' as a new and distinct cultivar of New Guinea *Impatiens* plant:

1. Single type medium purple-colored flowers;
2. Medium green-colored foliage; and
3. Vigorous, upright-mounded growth habit.

Plants of the new cultivar differ from plants of the female parent primarily in flower color and foliage color, and from plants of the male parent primarily in flower color and foliage color.

Of the many commercially available New Guinea *Impatiens* cultivars known to the inventor, the most similar in comparison to the new cultivar is Celebration Purple 'BFP-661 Purple', U.S. Plant Pat. No. 10,092. However, in side by side comparisons, plants of the new cultivar differ from plants of 'BFP-661 Purple' in the following characteristics:

1. Plants of the new cultivar have fewer flowers than plants of 'BFP-661 Purple'; and
2. Plants of the new cultivar have larger flowers than plants of 'BFP-661 Purple'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelimpur'. The plants were grown in 4.5 inch pots for 12 weeks in a greenhouse at West Chicago, Ill.

DETAILED BOTANICAL DESCRIPTION

Figure 1:
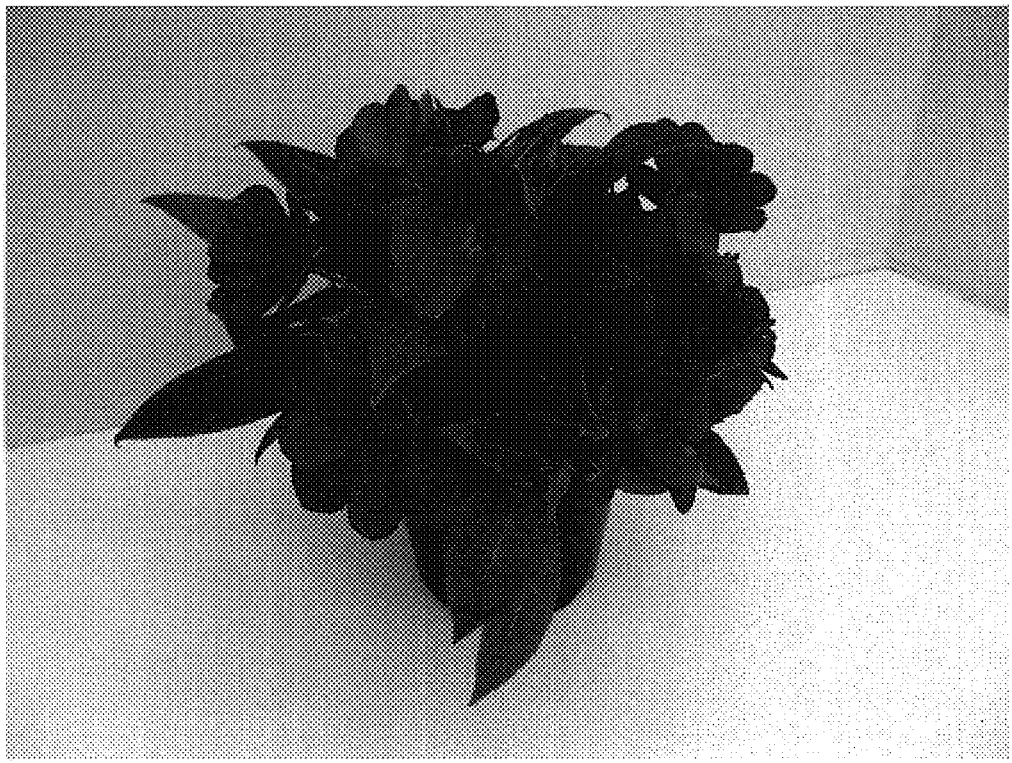
FIG. 1 illustrates a side view of the overall growth and flowering habit of 'Balcelimpur'.
Figure 2:
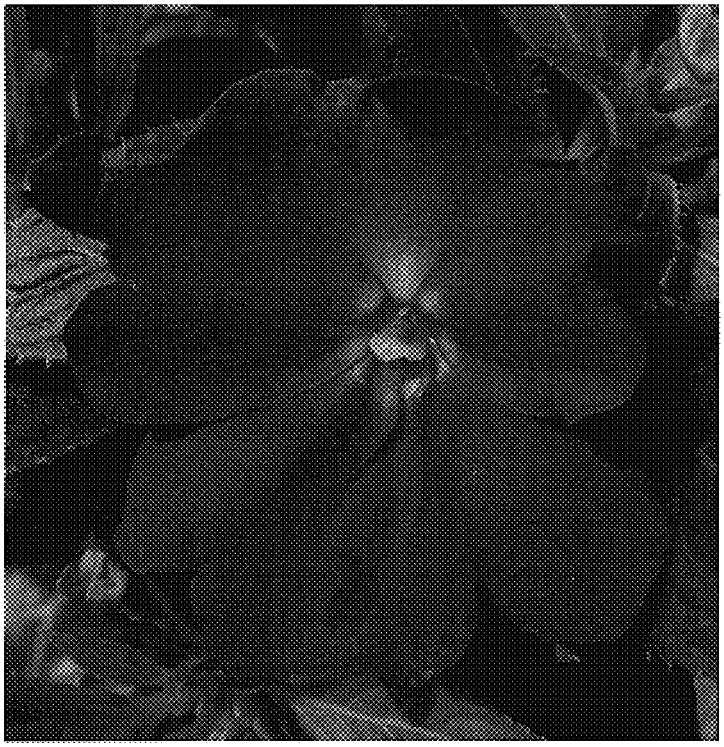
FIG. 2 illustrates a close-up view of an individual flower of 'Balcelimpur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 26, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 12 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens hawkeri* cultivar Balcelimpur.

Parentage:

*Female parent.*—Harmony Lavender Purple 'Danharpl', U.S. Plant Pat. No. 12,094.

*Male parent.*—Celebration Raspberry Rose 'Raspberry Rose', U.S. Plant Pat. No. 9,212.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 7 to 9 weeks from a rooted cutting.

*Growth habit and general appearance.*—Vigorous, upright-mounded.

*Size.*—Height from soil level to top of plant plane: Approximately 14.7 cm. Width: Approximately 24.4 cm.

*Branching habit.*—Freely basal branching. Quantity of main branches per plant: Approximately 6.

*Branch.*—Strength: Strong. Length: Approximately 9.0 cm. Diameter: Approximately 5.6 mm. Length of central internode: Approximately 1.7 cm. Texture: Glabrous. Color of young stem: 144C. Color of mature stem: 144C with a faint overlay of 185B.

Foliage description:

*General description.*—Quantity of leaves per main branch: Approximately 7. Fragrance: None. Form: Simple. Arrangement: In whorls of 3 to 5 leaves.

*Leaves.*—Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 9.0 cm. Width of mature leaf at center of stem: Approximately 3.8 cm. Texture of upper and lower surfaces: Glabrous. Color of upper surface of young foliage: 137A with venation of 145C. Color of lower surface of young and mature foliage: Closest to 138B with venation of 145B. Color of upper surface of mature foliage: 137A with venation of 145C and a faint overlay of 185B on lower half of midvein.

*Petiole.*—Length: Approximately 2.9 cm. Diameter: Approximately 3.7 mm. Texture: Glabrous. Color: Between 145B and 145C.

Flowering description:

*Flowering habit.*—'Balcelimpur' is freely flowering under outdoor growing conditions with substantially continuous blooming from spring through autumn and year-round in greenhouse environment.

*Lastingness of individual flower on the plant.*—Approximately 9 to 11 days.

Flower description:

*General description.*—Type: Single. Quantity per plant: Approximately 10. Fragrance: None.

*Bud.*—Rate of opening: Generally takes 3 to 4 days for bud to progress from first color to fully open flower. Quantity showing color per plant: Approximately 2.

*Bud just before opening.*—Shape: Ovoid. Length: Approximately 2.0 cm. Diameter: Approximately 1.3 cm. Color: Darker than N74A.

*Corolla.*—Shape: Round, cupped when first open with petals turning downward with age. Width: Approximately 7.2 cm. Depth: Approximately 1.9 cm. Borne: Above and below foliage.

*Petals.*—Quantity: 5. Shape: Obovate. Aspect: Flat. Appearance: Indescent. Margin: Entire. Apex: Emarginate. Base of upper petal: Truncate. Base of lateral and lower petals: Attenuate. Length of upper petal: Approximately 3.1 cm. Width of upper petal: Approximately 5.1 cm. Length of lateral petals: Approximately 3.4 cm. Width of lateral petals: Approximately 2.9 cm. Length of lower petals: Approximately 3.8 cm. Width of lower petals: Approximately 3.6 cm. Texture of upper and lower surfaces: Glabrous. Color of upper surface when first and fully open: Darker than N74A fading to 75C near base; lateral and lower petals have an eye of 53C. Color of lower surface when first and fully open: N74B.

*Spur.*—Quantity: 1 per flower. Length: Approximately 5.8 cm. Diameter at tip: Approximately 1.0 mm. Diameter at base: Approximately 3.0 mm. Texture: Glabrous. Color: 187C and tip of 144C.

*Peduncle.*—Strength: Strong. Aspect: Acute angle to stem. Length: Approximately 4.4 cm. Diameter: Approximately 2.0 mm. Texture: Glabrous. Color: 144C with a faint overlay of 185B.

*Sepals.*—Quantity per flower: 4, with one fused to base of upper petal. Shape of lateral sepals: Ovate. Shape of lower sepal: Ovate. Apex of all sepals: Acuminate. Length of lateral sepals: Approximately 1.3 cm. Width of lateral sepals: Approximately 6.6 mm. Length of lower sepal: Approximately 1.6 cm. Width of lower sepal: Approximately 1.4 cm. Texture of upper and lower surfaces of all sepals: Glabrous. Color of lateral sepals: 145D with a faint overlay of 185C and tip of 144B. Color of lower sepal: N155B with an overlay of 186C and tip of 144B.

*Reproductive organs.*—Androecium: Stamen quantity: 5 per flower, fused around pistil at apex. Anther shape: Hooded. Anther length: Approximately 3.0 mm. Anther color: Lighter than 160D at apex transitioning to N66A toward filament. Filament color: N66A. Pollen amount: Abundant. Pollen color: 155D. Gynoecium: Pistil quantity: 1 per flower. Pistil length: Approximately 4.0 mm. Stigma shape: 5-pointed star. Stigma color: Colorless, transparent. Style color: 144B. Ovary texture: Glabrous. Ovary color: 144B.

Seed and fruit production: Neither seed nor fruit production has been observed.

Disease and pest resistance: Resistance to pathogens and pests common to New Guinea New Guinea *Impatiens* has not been observed.

What is claimed is:

1. A new and distinct cultivar of New Guinea *Impatiens* plant named 'Balcelimpur', substantially as herein shown and described.

* * * * *